US009320679B2

(12) United States Patent
Lee

(10) Patent No.: US 9,320,679 B2
(45) Date of Patent: Apr. 26, 2016

(54) MOXIBUSTION DEVICE

(75) Inventor: Kin Ming Lee, Hong Kong (CN)

(73) Assignee: Traditional Chinese Medical Centre Limited, Hong Kong (CN)

( * ) Notice: Subject to any disclaimer, the term of this patent is extended or adjusted under 35 U.S.C. 154(b) by 952 days.

(21) Appl. No.: 13/551,623

(22) Filed: Jul. 18, 2012

(65) Prior Publication Data

US 2013/0018443 A1 Jan. 17, 2013

(30) Foreign Application Priority Data

Jul. 15, 2011 (HK) .................................... 11107402

(51) Int. Cl.

| | |
|---|---|
| ***A61B 18/06*** | (2006.01) |
| ***A61H 39/04*** | (2006.01) |
| ***A61H 39/06*** | (2006.01) |
| *A61H 15/00* | (2006.01) |

(52) U.S. Cl.

CPC ................ *A61H 39/04* (2013.01); *A61H 39/06* (2013.01); *A61H 2015/0014* (2013.01)

(58) Field of Classification Search

CPC .................. A61H 39/06; A61H 15/02; A61H 2015/0014; A61B 2018/064

USPC ............................................. 601/19; 607/114

See application file for complete search history.

(56) References Cited

U.S. PATENT DOCUMENTS

| | | | | |
|---|---|---|---|---|
| 1,817,823 | A * | 8/1931 | Ito | 604/24 |
| 4,731,050 | A * | 3/1988 | Harada et al. | 604/24 |
| 5,931,806 | A * | 8/1999 | Shimada | 604/24 |
| 7,160,315 | B2 * | 1/2007 | Cheng | 607/96 |
| 2004/0019305 | A1 * | 1/2004 | Tu | 601/107 |
| 2011/0319818 | A1 * | 12/2011 | Shimada et al. | 604/114 |
| 2013/0012848 | A1 * | 1/2013 | Forrest | 601/19 |
| 2013/0231594 | A1 * | 9/2013 | Bennett | 601/19 |
| 2013/0281894 | A1 * | 10/2013 | Ling | 601/19 |

FOREIGN PATENT DOCUMENTS

| | | | |
|---|---|---|---|
| CN | 201098249 | Y * | 8/2008 |
| CN | 101926728 | A * | 12/2010 |
| CN | 101933885 | A * | 1/2011 |

* cited by examiner

*Primary Examiner* — Joseph Stoklosa
*Assistant Examiner* — Jocelyn D Ram

(57) ABSTRACT

A moxibustion device includes a handle, a moxa stick clamping unit, a front fixing component, a front rolling ring, a front roller cover, a traditional Chinese medicine (moxa stick), a back roller cover, a back bearing, a back fixing component, a roller's inner screen and a rotary drum. The moxibustion device is of a more ergonomic design and allows for more accurate and more direct application of force and/or rolling on acupuncture points; it is applicable to the parts of body with a small bending scope such as joints of the limbs and cervical vertebra and large-area skin such as the waist and the back. It can be easily operated, and the acupuncture points and the main and collateral channels can be acutely located.

8 Claims, 10 Drawing Sheets

C-C

C-C

MOXIBUSTION DEVICE

BACKGROUND OF THE PRESENT INVENTION

1. Field of Invention

The present invention relates to a moxibustion device for external disease treatment and healthcare.

2. Description of Related Arts

The traditional moxibustion device comprises a metal cylinder with a moxa stick inside, and one end of the cylinder is provided with a metal screen. When this kind of moxibustion device is used, the positioning of the burning head shall be adjusted randomly to keep burning, and the ashes are discharged via holes (there is only one single metal screen and the meshes are large, so it scalds easily and drops ashes). The traditional moxibustion devices are usually provided with a handle at one end, which applies uneven force onto the compressed position, which means that the force applied onto the front part is smaller than that onto the rear part.

SUMMARY OF THE PRESENT INVENTION

The objective of the present invention is to overcome defects of the existing moxibustion device and provide a moxibustion device with a new structure.

The present invention adopts the following technical scheme: the moxibustion device comprises a handle, a traditional Chinese medicine clamping unit, a front fixed component, a front rolling ring, a front roller cover, traditional Chinese medicines, a rear roller cover, a rear bearing, a rear fixed component, a roller's inner screen and a rotary drum, wherein the front fixed component and the rear fixed component are respectively connected to two ends in the handle, wherein the front fixed component is provided with the front rolling ring inside; the front rolling ring is provided with the front roller cover inside; the front roller cover rotates in the front rolling ring; one end of the roller's inner screen is sleeved on the front roller cover; the traditional Chinese medicine clamping unit clamps the traditional Chinese medicine so that it passes through the front fixed component and the front roller cover; the traditional Chinese medicines are placed in the roller's inner screen; the traditional Chinese medicine clamping unit is connected with the front fixed component; the traditional Chinese medicine clamping unit and the front roller cover rotate with respect to each other, wherein the rear fixed component is fixed with the rear bearing; an inner ring of the rear bearing is fixed with the rear roller cover; the rear roller cover rotates in the rear bearing; the other end of the roller's inner screen is sleeved on the rear roller cover; and the roller's inner screen is sleeved with the rotary drum outside.

The technical scheme also comprises:

The front fixed component comprises a round fixed seat; the fixed seat is provided with a step-like fixed block; the fixed block has a through-hole inside; the through-hole is uniformly formed with clamping slots inside; and the traditional Chinese medicine clamping unit passes through the through-hole.

The rear fixed component comprises a round fixed seat; the fixed seat is provided with a step-like fixed block; the fixed block has a blind hole inside; the blind hole is uniformly formed with raised strips inside; and the blind hole is provided with the rear bearing inside.

The traditional Chinese medicine clamping unit comprises a shaft sleeve; one end of the shaft sleeve is a plummer block; an external spherical surface of the shaft sleeve is uniformly provided with projections; the projections are respectively fixed with elastic traditional Chinese medicine clamping pieces; the elastic traditional Chinese medicine clamping pieces are used for clamping the traditional Chinese medicines; the projections are matched with the clamping slots of the front fixed component.

The front roller cover comprises a middle plummer block; a shaft shoulder and a flange are located on both sides of the middle plummer block respectively, wherein the flange contacts the front rolling ring, while the shaft shoulder is connected with the roller's inner screen and the rotary drum.

The rear roller cover comprises a middle plummer block; a shaft shoulder and a flange are located on both sides of the middle plummer block respectively, wherein the flange is connected with the roller's inner screen and the rotary drum, while the shaft shoulder is fixed with the inner ring of the rear bearing.

Both ends of an inner wall of the handle are respectively provided with step-like fixing grooves for fixing the step-like fixing blocks of the front fixed component and the rear fixed component.

The roller's inner screen is uniformly provided with round meshes, and the rotary drum is uniformly provided with strip-like meshes.

The traditional Chinese medicines include moxa sticks.

The present invention has the advantages that: the moxibustion device is of ergonomic design and can be accurately and directly pressed and/or rolled on acupuncture points; it is applicable to the parts of body with a small bending scope such as joints of the limbs and cervical vertebra and large-area skin such as the waist and back. It can be easily operated, the acupuncture points and the main and collateral channels can be acutely located; the ash leakage is avoided; and it is more convenient to replace the moxa stick.

As shown in the figure: 1, handle; 11, step-like fixing groove; 12, screw hole; 2, traditional Chinese medicine clamping unit; 21, shaft sleeve; 22, projection; 23, plummer block; 3, front fixed component; 31, fixed seat; 32, step-like fixed block; 33, clamping slot; 34, through-hole; 4, front rolling ring; 5, front roller cover; 51, flange; 52, middle plummer block; 53, shaft shoulder; 6; traditional Chinese medicines; 7, rear roller cover; 8, rear bearing; 9; rear fixed component; 91, blind hole; 92, raised strip; 10, roller's inner screen; 101, round mesh; 20, rotary drum; 201, strip-like mesh; 30, elastic traditional Chinese medicine clamping plate; 40, bracket; 401 groove.

DETAILED DESCRIPTION OF THE PREFERRED EMBODIMENT

The present invention is further described in details with the references of the attached drawings.

Figure 1:
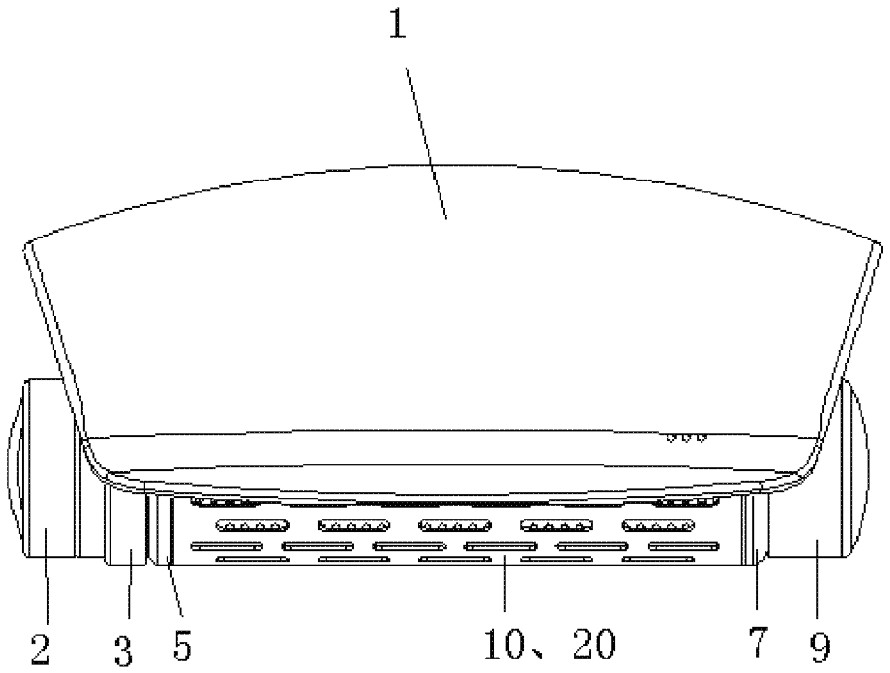
FIG. 1 is a front view of the whole structure of the present invention.
Figure 2:
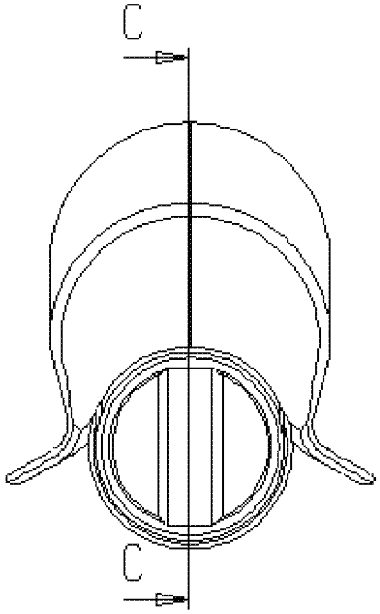
FIG. 2 is a left view of the FIG. 1.
Figure 3:
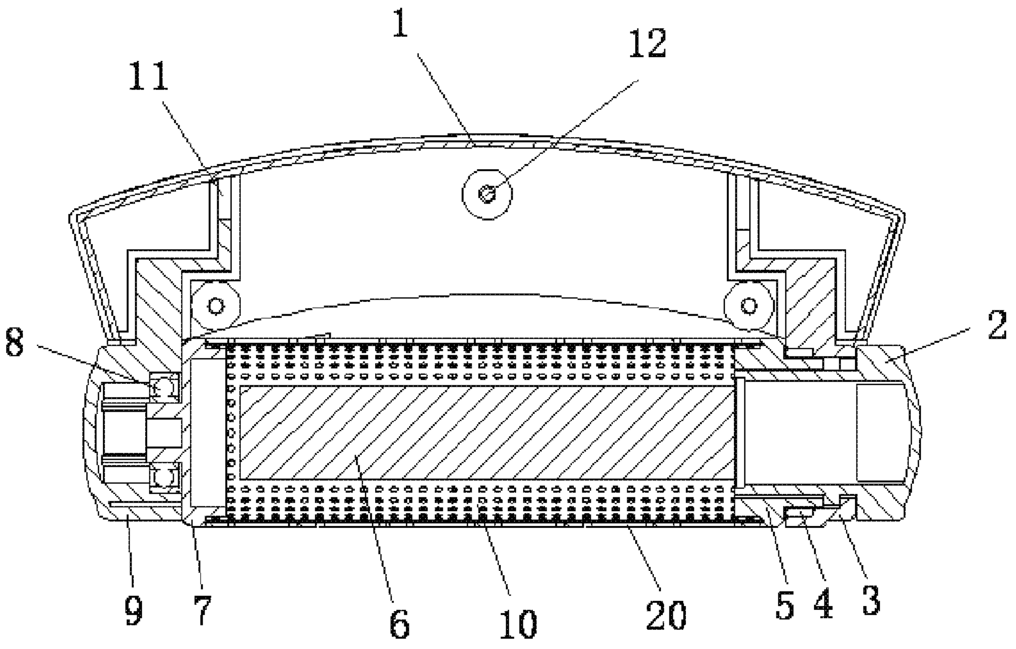
FIG. 3 is a C-C sectional view of the FIG. 2.
Figure 4:
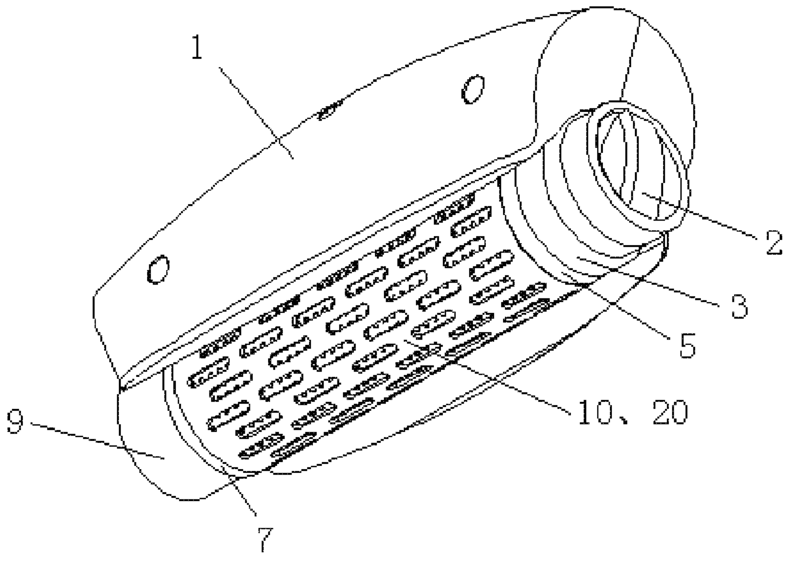
FIG. 4 is a three-dimensional view of the FIG. 1.
Figure 5:
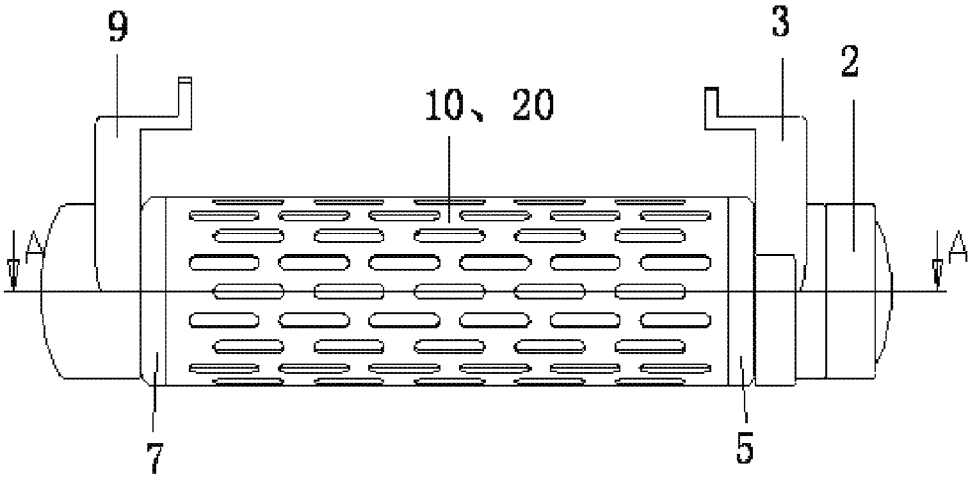
FIG. 5 is a schematic view of the assembly of the FIG. 1 without the handle.
Figure 6:
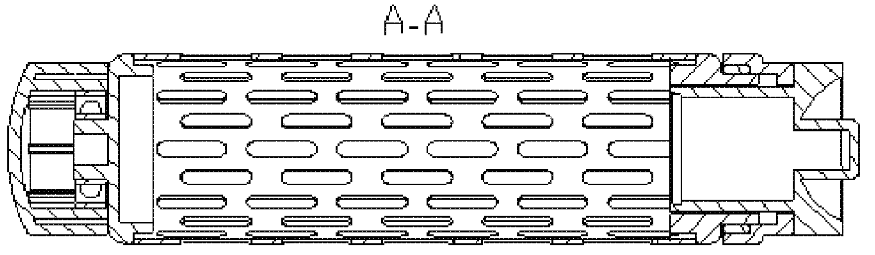
FIG. 6 is an A-A sectional view of the FIG. 5.
Figure 7:
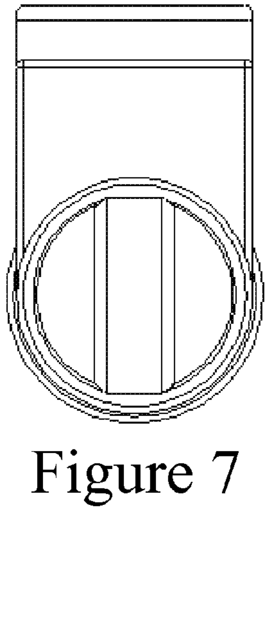
FIG. 7 is a right view of the FIG. 6.
Figure 8:
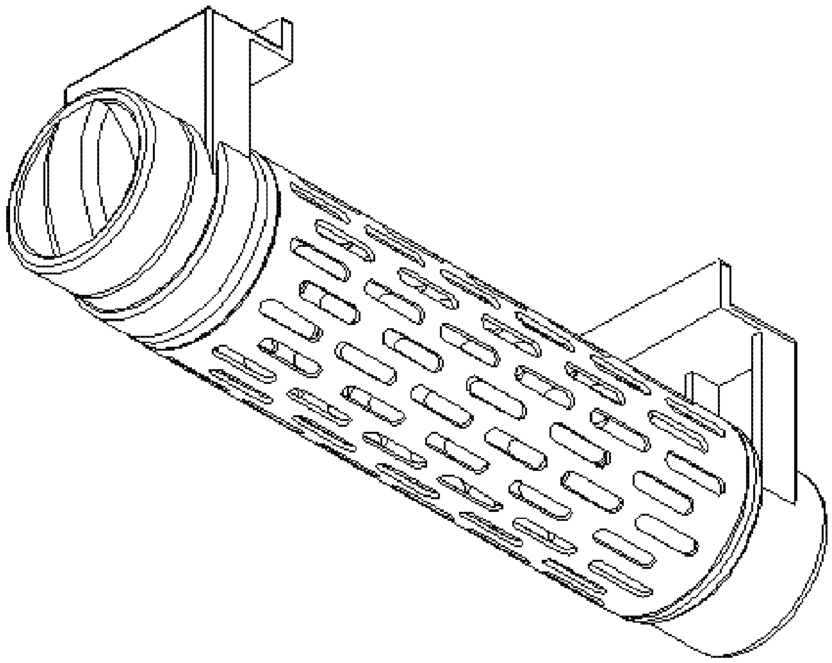
FIG. 8 is a three-dimensional view of the FIG. 5.
Figure 9:
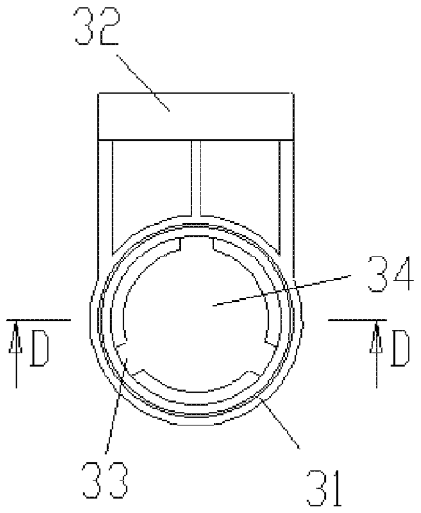
FIG. 9 is a front view of a front fixed component as shown in FIG. 1.
Figure 10:
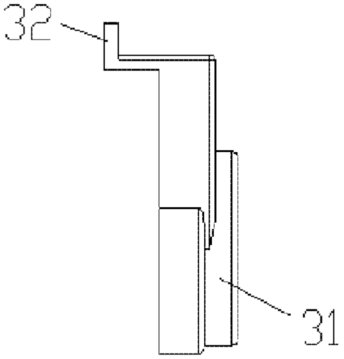
FIG. 10 is a right view of the FIG. 9.
Figure 11:
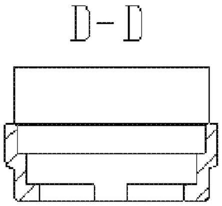
FIG. 11 is a D-D sectional view of the FIG. 9.
Figure 12:
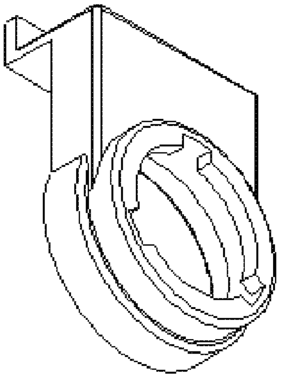
FIG. 12 is a three-dimensional view of the FIG. 9.
Figure 13:
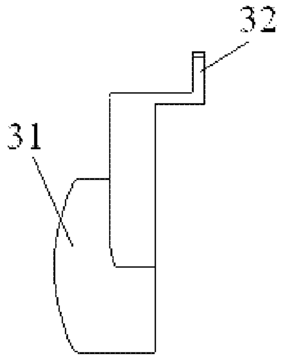
FIG. 13 is a front view of a rear fixed component as shown in FIG. 1.
Figure 14:
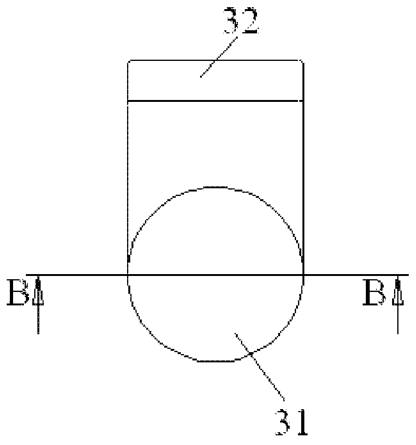
FIG. 14 is a left view of the FIG. 13.
Figure 15:
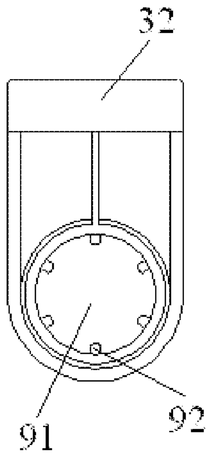
FIG. 15 is a right view of the FIG. 13.
Figure 16:
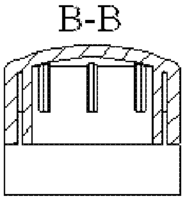
FIG. 16 is a B-B sectional view of the FIG. 14.
Figure 17:
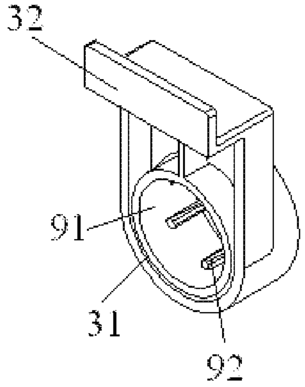
FIG. 17 is a three-dimensional view of the FIG. 13.
Figure 18:
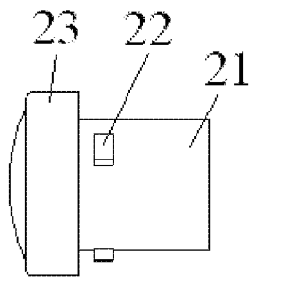
FIG. 18 is a front view of a traditional Chinese medicine clamping unit as shown in FIG. 1.
Figure 19:
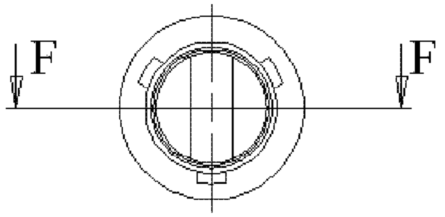
FIG. 19 is a right view of the FIG. 18.
Figure 20:
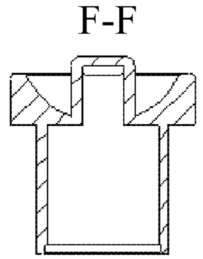
FIG. 20 is an F-F sectional view of the FIG. 19.
Figure 21:
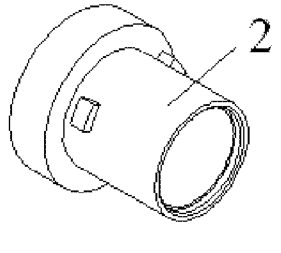
FIG. 21 is a three-dimensional view of the FIG. 18.

As shown in FIG. 1, the moxibustion device consists of a handle 1 (plastic), a traditional Chinese medicine (moxa stick) clamping unit 2 (plastic or metal plate), a front fixed component 3 (plastic or alloy), a front rolling ring 4 (nylon), a front roller cover 5 (alloy), traditional Chinese medicines 6 (moxa stick or other traditional Chinese medicine formulas), a rear roller cover 7 (alloy), a rear bearing 8 (alloy), a rear fixed component 9 (plastic or alloy), a roller's inner screen 10 (metal), and a rotary drum 20 (metal).

Figure 31A:
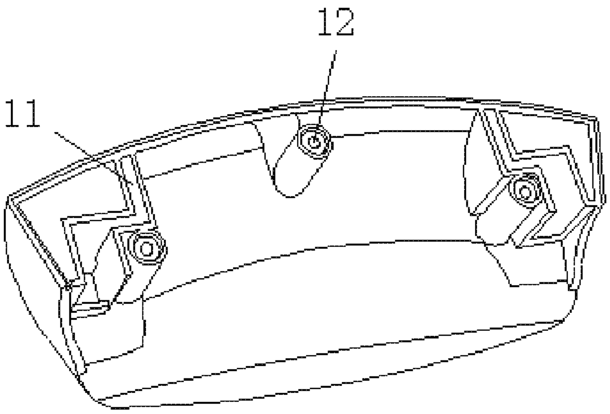
FIGS. 31*a* and 31*b* are two three-dimensional views of a handle as shown in the FIG. 1.
Figure 31B:
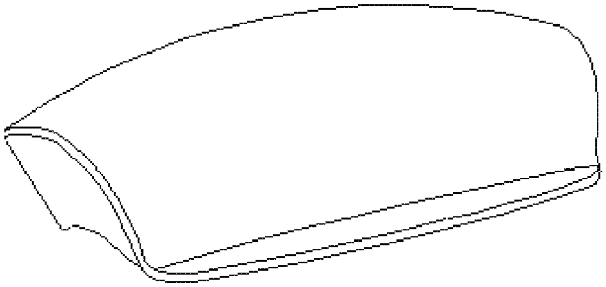
Figure 32:
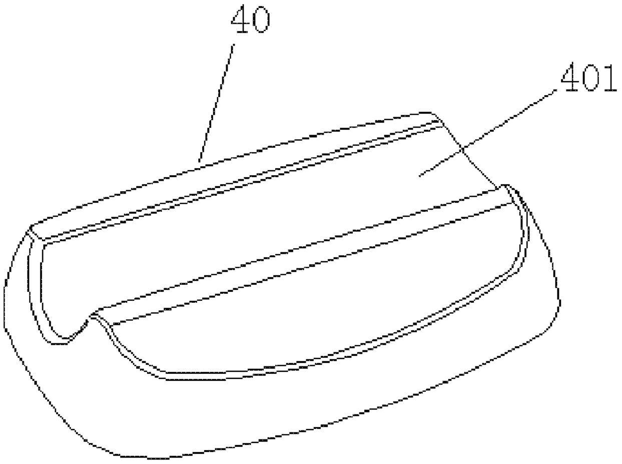
FIG. 32 is a three-dimensional view of a bracket in the present invention.

The handle 1 (as shown in FIG. 31) consists of two parts; the bottom is recessed; the two ends of the inner wall are respectively provided with a step-like fixing groove 11 for fixing the front fixed component 3 and the rear fixed component 9; screw holes 12 are formed in the rear; and the two parts of the handle are connected with a screw.

The front fixed component 3 (as shown in FIGS. 9-12) comprises a round fixed seat 31 provided with a step-like fixed block 32; the round fixed seat 31 has a through-hole 34 inside; the through-hole 34 is uniformly formed with three clamping slots 33; the traditional Chinese medicine clamping unit 2 passes through the through-hole 34; the front fixed component 3 is fixed in the step-like fixing groove 11 of the handle 1 via the step-like fixing block 32.

The rear fixed component 9 (as shown in FIGS. 13-17) comprises a round fixed seat 31 provided with a step-like fixed block 32; the round fixed seat 31 has a blind hole 91 inside; the blind hole 91 is uniformly formed with six raised strips 92; and the rear fixed component 9 is fixed in the step-like fixing groove 11 of the handle 1 via the step-like fixing block 32.

Figure 26:
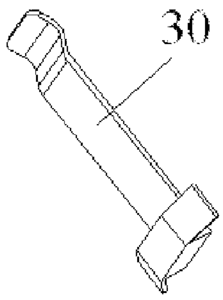
FIG. 26 is a three-dimensional view of an elastic traditional Chinese medicine clamping plate as shown in FIG. 1.

The traditional Chinese medicine clamping unit 2 (as shown in FIGS. 18-21) comprises a shaft sleeve 21; one end of the shaft sleeve 21 is a plummer block 23; the outer surface of the shaft sleeve 21 is uniformly provided with three projections 22; each projection 22 is fixed with an elastic traditional Chinese medicine clamping plate 30 (as shown in FIG. 26) for clamping the traditional Chinese medicines 6 (such as moxa stick); and the projections 22 are matched with the clamping slots 33 of the front fixed component 3.

Figure 22:
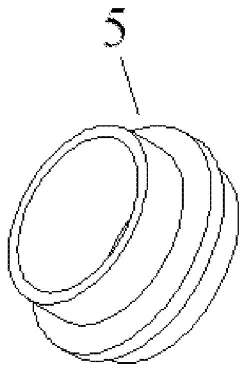
FIG. 22 is a three-dimensional view of a front roller cover as shown in the FIG. 1.
Figure 23:
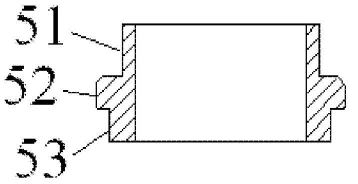
FIG. 23 is a sectional view of the FIG. 22.
Figure 27:
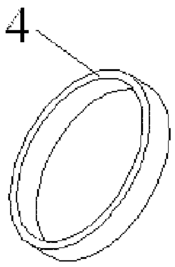
FIG. 27 is a three-dimensional view of a front rolling ring as shown in the FIG. 1.
Figure 29:
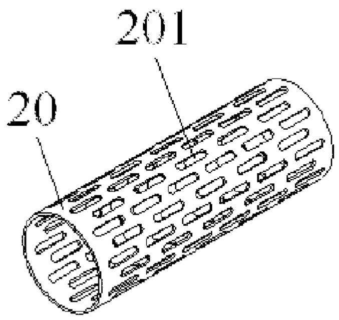
FIG. 29 is a three-dimensional view of a rotary drum as shown in the FIG. 1.
Figure 30:
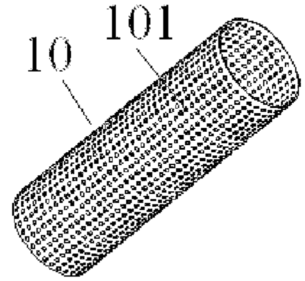
FIG. 30 is a three-dimensional view of a roller's inner screen as shown in the FIG. 1.

The front roller cover 5 (as shown in FIGS. 22-23) comprises a middle plummer block 52; a shaft shoulder 53 and a flange 51 are respectively located on both sides of the middle plummer block 52; the flange 51 contacts the front rolling ring 4 (as shown in FIG. 27), while the shaft shoulder 53 is connected with the roller's inner screen 10 and the rotary drum 20 (as shown in FIGS. 29-30).

Figure 24:
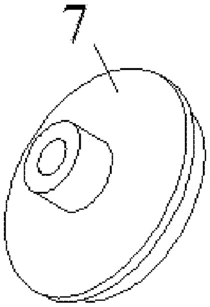
FIG. 24 is a three-dimensional view of a rear roller cover as shown in the FIG. 1.
Figure 25:
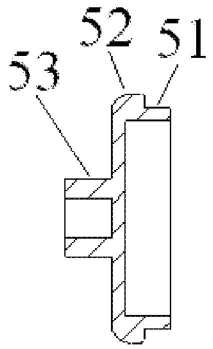
FIG. 25 is a sectional view of the FIG. 24.
Figure 28:
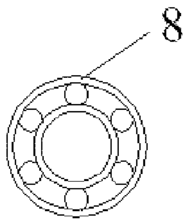
FIG. 28 is a three-dimensional view of a rear bearing as shown in the FIG. 1.

The rear roller cover 7 (as shown in FIGS. 24-25) comprises a middle plummer block 52; a shaft shoulder 53 and a flange 51 are located on both sides of the middle plummer block respectively 52; the flange 51 is connected with the roller's inner screen 10 and the rotary drum 20, while the shaft shoulder 53 is fixed together with the inner ring of the rear bearing 8 (as shown in FIG. 28).

The through-hole 34 of the front fixed component 3 is provided with the front rolling ring 4 inside; the front rolling ring 4 is provided with the front roller cover 5 inside; the front roller cover 5 rotates in the front rolling ring 4; one end of the roller's inner screen 10 is sleeved on the shaft shoulder 53 of the front roller cover 5; the traditional Chinese medicine clamping unit 2 clamps the traditional Chinese medicines 6 to pass through the front fixed component 3 and the front roller cover 5; the traditional Chinese medicines 6 are placed in the roller's inner screen 10; the traditional Chinese medicine clamping unit 2 is connected with the front fixed component 3; and the traditional Chinese medicine clamping unit 2 and the front roller cover 5 rotate with respect to each other; the blind hole 91 of the rear fixed component 9 is installed with the rear bearing 8 inside; the inner ring of the rear bearing 8 is fixed together with the rear roller cover 7; the rear roller cover 7 rotates in the rear bearing 8; the other end of the roller's inner screen 10 is sleeved on the flange 51 of the rear roller cover 7. The roller's inner screen 10 is externally sleeved with the rotary drum 20.

The surface of the roller's inner screen 10 is uniformly formed with dense round meshes 101 to avoid ash leakage. The surface of the rotary drum 20 is uniformly provided with strip-like meshes 201 to improve the thermal energies and drug effect of the traditional Chinese medicines.

The surface of the bracket 40 is formed with a groove 401 on which the moxibustion device can be placed in case of non-use.

Working principle:

The burning moxa stick 6 is clamped at the front end of the traditional Chinese medicine clamping unit 2; and then the traditional Chinese medicine clamping unit 2 is inserted into the hole of the front fixed component 3. When replacing the moxa stick 6, the traditional Chinese medicine clamping unit 2 is pulled out to replace a new moxa stick 6 without touching the hot metal part, and the position of the burning head is not required to be adjusted in use.

The moxibustion device has the characteristics that: it is of ergonomic design and can be accurately and directly pressed and/or rolled on acupuncture points; it is applicable to the parts of body with a small bending scope such as joints of the limbs and cervical vertebra and large-area skin such as the waist and back; it can be easily operated, the acupuncture points and the main and collateral channels can be acutely located.

What is claimed is:

1. A moxibustion device, comprising:

a handle, a clamping unit, a front fixed component, a front rolling ring, a front roller cover, moxa sticks, a rear roller cover, a rear bearing, a rear fixed component, a roller's inner screen and a rotary drum, wherein the front fixed component and the rear fixed component are respectively connected to two ends in the handle, wherein the front fixed component is provided with the front rolling ring inside; the front rolling ring is provided with the front roller cover inside; the front roller cover rotates in the front rolling ring; one end of the roller's inner screen is sleeved on the front roller cover; the clamping unit clamps the moxa sticks and passes through the front fixed component and the front roller cover; the moxa sticks are placed in the roller's inner screen; the clamping unit is connected with the front fixed component; the clamping unit and the front roller cover rotate with respect to each other;

wherein the rear fixed component is fixed with the rear bearing; an inner ring of the rear bearing is fixed with the rear roller cover; the rear roller cover rotates in the rear bearing; the other end of the roller's inner screen is sleeved on the rear roller cover; and the roller's inner screen is sleeved with the rotary drum outside;

wherein the front fixed component comprises a fixed seat; the fixed seat is provided with a stepped fixed block; the fixed block has a through-hole inside; the through-hole is uniformly formed with clamping slots inside; and the clamping unit passes through the through-hole.

2. The moxibustion device according to claim 1, wherein the clamping unit comprises a shaft sleeve; one end of the shaft sleeve is a plummer block; an external surface of the shaft sleeve is uniformly provided with projections; the projections are respectively fixed with elastic clamping plates; the elastic clamping plates are used for clamping the moxa sticks; the projections are matched with the clamping slots of the front fixed component.

3. The moxibustion device according to claim 1, wherein the front roller cover comprises a middle plummer block; a shaft shoulder and a flange are respectively located on both sides of the middle plummer block, wherein the flange contacts the front rolling ring, while the shaft shoulder is connected with the roller's inner screen and the rotary drum.

4. The moxibustion device according to claim 1, wherein the rear roller cover comprises a middle plummer block; a shaft shoulder and a flange are respectively located on both sides of the middle plummer block, wherein the flange is connected with the roller's inner screen and the rotary drum, while the shaft shoulder is fixed with the inner ring of the rear bearing.

5. The moxibustion device according to claim 1, wherein two ends of an inner wall of the handle are respectively provided with stepped fixing grooves, the stepped fixing groove at one end is adapted for fixing the stepped fixing block of the front fixed component.

6. The moxibustion device according to claim 1, wherein the roller's inner screen is uniformly provided with round meshes, and the rotary drum is uniformly provided with strip-shaped meshes.

7. A moxibustion device, comprising:

a handle, a clamping unit, a front fixed component, a front rolling ring, a front roller cover, moxa sticks, a rear roller cover, a rear bearing, a rear fixed component, a roller's inner screen and a rotary drum, wherein the front fixed component and the rear fixed component are respectively connected to two ends in the handle, wherein the front fixed component is provided with the front rolling ring inside; the front rolling ring is provided with the front roller cover inside; the front roller cover rotates in the front rolling ring; one end of the roller's inner screen is sleeved on the front roller cover; the clamping unit clamps the moxa sticks and passes through the front fixed component and the front roller cover; the moxa sticks are placed in the roller's inner screen; the clamping unit is connected with the front fixed component; the clamping unit and the front roller cover rotate with respect to each other;

wherein the rear fixed component is fixed with the rear bearing; an inner ring of the rear bearing is fixed with the rear roller cover; the rear roller cover rotates in the rear bearing; the other end of the roller's inner screen is sleeved on the rear roller cover; and the roller's inner screen is sleeved with the rotary drum outside;

wherein the rear fixed component comprises a fixed seat; the fixed seat is provided with a stepped fixed block; the fixed block has a blind hole inside; the blind hole is uniformly formed with raised strips; and the blind hole is provided with the rear bearing inside.

8. The moxibustion device according to claim 7, wherein two ends of an inner wall of the handle are respectively provided with stepped fixing grooves, the stepped fixing groove at one end is adapted for fixing the stepped fixing block of the rear fixed component.

* * * * *